(12) United States Patent
Agrawal et al.

(10) Patent No.: US 8,731,738 B2
(45) Date of Patent: May 20, 2014

(54) POWERED MOBILITY SYSTEMS AND METHODS

(75) Inventors: Sunil K. Agrawal, Newark, DE (US); James C. Galloway, Elkton, MD (US); Xi Chen, Newark, DE (US); Christina B. Ragonesi, Newark, DE (US); Sherry Liang, Staten Island, NY (US); Stephen Dolph, New Carlisle, IN (US); Zachary R. Schoepflin, Centerport, NY (US)

(73) Assignee: University of Delaware, Newark, DE (US)

( * ) Notice: Subject to any disclaimer, the term of this patent is extended or adjusted under 35 U.S.C. 154(b) by 233 days.

(21) Appl. No.: 13/222,437

(22) Filed: Aug. 31, 2011

(65) Prior Publication Data
US 2012/0059548 A1 Mar. 8, 2012

Related U.S. Application Data

(60) Provisional application No. 61/378,631, filed on Aug. 31, 2010, provisional application No. 61/386,216, filed on Sep. 24, 2010.

(51) Int. Cl.
*G05D 1/00* (2006.01)

(52) U.S. Cl.
USPC .............................................. 701/1

(58) Field of Classification Search
CPC ................... B62D 6/00; G01C 22/00
USPC .............. 701/1, 23, 25, 26, 28, 538
See application file for complete search history.

(56) References Cited

U.S. PATENT DOCUMENTS

| | | | |
|---|---|---|---|
| 4,796,903 A | 1/1989 | Proctor | |
| 5,592,997 A | 1/1997 | Ball | |
| 5,701,968 A | 12/1997 | Wright-Ott | |
| 6,154,690 A | 11/2000 | Coleman | |
| 6,771,034 B2 * | 8/2004 | Reile et al. | 318/139 |
| 7,182,351 B2 | 2/2007 | Williams | |
| 2002/0038942 A1 | 4/2002 | Gilles | |

(Continued)

FOREIGN PATENT DOCUMENTS

| | | |
|---|---|---|
| KR | 20030039084 A | 5/2003 |
| WO | WO2009/072126 A2 | 6/2009 |

OTHER PUBLICATIONS

International Application Serial No. PCT/US08/78726, International Search Report mailed Dec. 5, 2008, 2 pgs.

(Continued)

*Primary Examiner* — Kim T Nguyen
(74) *Attorney, Agent, or Firm* — RatnerPrestia

(57) ABSTRACT

Powered mobility systems and methods are disclosed. A powered mobility system includes a mobile unit, a support frame, a plurality of markers, a motion capture device, and a processor. The mobile unit is operable to move the powered mobility system. The support frame is adapted to support a user. The plurality of markers are configured to be attached to the user. The motion capture device is configured to detect movement of the plurality of markers. The processor is programmed to receive signals from the motion capture device, translate the signals into instructions for moving the mobile unit, and transmit the instructions to the mobile unit. A powered mobility method includes placing a user in a support frame, attaching a plurality of markers to the user, detecting movement of the plurality of the markers, and generating movement of the mobile unit based on the movement of the plurality of the markers.

20 Claims, 3 Drawing Sheets

(56) References Cited

U.S. PATENT DOCUMENTS

| | | | |
|---|---|---|---|
| 2004/0267442 A1 | 12/2004 | Fehr | |
| 2005/0183900 A1 | 8/2005 | Goertzen | |
| 2006/0011393 A1 | 1/2006 | Bergum | |
| 2009/0121532 A1 | 5/2009 | Kruse | |
| 2009/0132124 A1* | 5/2009 | Agrawal et al. | 701/41 |

OTHER PUBLICATIONS

International Application Serial No. PCT/US08/78726, International Written opinion mailed Dec. 5, 2008, 4 pgs.

"NF-Walker User Manual", Made for Movement Copyright 2011, 20 Pgs.

Agrawal, Sunil K., "Training Special Needs Infants to Drive Mobile Robots Using Force-Feedback Joystick", Robotics and Automation (ICRA), 2010 IEEE International Conference on (May 3-7, 2010), 4797-4802.

Chen Xi, "Design of a Novel Mobility Interface for Infants on a Mobile Robot by Kicking", Journal of Medical Devices, vol. 4 (Sep. 2010), 031006-1/031006-5.

Galloway, James C., "Babies Driving Robots: Self-Generated Mobility in Very Young Infants", Intelligent Service Robotics, vol. 1, No. 2. doi:10.1007/s11370-007-0011-2 , (Apr. 1, 2008), 123-134.

Mattern-Baxter Katrin, "Locomotor Treadmill Training for Children With Cerebral Palsy", Orthopaedic Nursing vol. 29 No. 3 (May/Jun. 2010), 169-173.

Schoepflin, Zachary R., "Design of a Novel Mobility Device Controlled by the Feet Motion of a Standing Child: A Feasibility Study", Med Biol Eng Comput (2011) 49:DOI 10,lOO7/sll517-011-0820-5, 1225-1231.

Schoepflin, Zachary R., "Design of a Novel Mobility Device Controlled by the Walking Action of a Standing Child", http://www.flintbox.com/public/prject/7604.

Schoepflin, Zachary R., "Design of a Novel Mobility Device Controlled by the Walking Action of a Standing Child", Rehabilitation Robotics (ICORR), 2011 IEEE International Conference (Jun. 29, 2011-Jul. 1, 2011), 16.

International Search Report dated May 1, 2012, application No. PCT/US2011/049891.

* cited by examiner

POWERED MOBILITY SYSTEMS AND METHODS

CROSS REFERENCE TO RELATED APPLICATIONS

This application claims priority to U.S. Patent Application No. 61/378,631, entitled "INTERFACE FOR CONTROLLING A ROBOT USING BODY MOVEMENT," filed on Aug. 31, 2010, and to U.S. Patent Application No. 61/386,216, entitled "MOBILITY DEVICE CONTROLLED BY MIMICKED WALKING ACTION OF USER," filed on Sep. 24, 2010, the contents of each of which are incorporated herein by reference in their entirety.

STATEMENT REGARDING FEDERALLY SPONSORED RESEARCH

The subject matter of the present invention was funded at least in part under National Science Foundation Grant No. NSF0745833 and National Institutes of Health Grant No. HD047468. The U.S. Government may have certain rights in this invention.

FIELD OF THE INVENTION

The present invention relates generally to mobility systems, and more particularly, to powered mobility systems for users lacking natural mobility.

BACKGROUND OF THE INVENTION

Self-generated mobility is a major contributor to the physical, emotional, cognitive, and social development of infants and toddlers. When young children have disorders that hinder self locomotion, their cognitive and psychological development is at risk for delay.

Many infants with special needs, such as with Down Syndrome, cerebral palsy, and autism, experience such a delay in their development of independent mobility due to weak musculature and/or poor coordination. Conventionally, in accordance with certain medical practices, these children may not use powered chairs until the age of five. As such, they spend considerably less time moving around in their environment compared to typically developing children of the same age. Lack of independent mobility may result in delays in their cognitive, perceptual, social, and emotional development, which are well correlated with locomotion.

Accordingly, there exists a need for systems that provide the ability for such children and other users to independently explore their world.

SUMMARY OF THE INVENTION

Aspects of the present invention relate to powered mobility systems and methods.

In accordance with one aspect of the present invention, a powered mobility system is disclosed. The powered mobility system includes a mobile unit, a support frame, a plurality of markers, a motion capture device, and a processor. The mobile unit is operable to move the powered mobility system. The support frame is coupled to the mobile unit. The support frame is adapted to support a user of the powered mobility system. The plurality of markers are configured to be attached to the user. The motion capture device is configured to detect movement of the plurality of markers. The processor is in communication with the motion capture device. The processor is programmed to receive signals from the motion capture device, translate the signals from the motion capture device into instructions for moving the mobile unit, and transmit the instructions to the mobile unit in order to move the powered mobility system.

In accordance with another aspect of the present invention, a powered mobility method is disclosed. The powered mobility method includes placing a user in a support frame, attaching a plurality of markers to the user, detecting movement of the plurality of the markers with a motion capture device when the plurality of markers are attached to the user, and generating movement of the mobile unit based on the movement of the plurality of the markers detected by the motion capture device.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings are not drawn to scale unless otherwise indicated. On the contrary, the dimensions of the various features may be expanded or reduced for clarity. Included in the drawings are the following figures.

DETAILED DESCRIPTION OF THE INVENTION

The various aspects of the present invention relate generally to systems and methods for permitting a user to navigate his or her environment. The disclosed embodiments include components that enable the user to generate and control his or her own movement through powered maneuvering of a mobile unit. The mobile unit is controlled by detecting the user's movements and then translating those movements into commands for the mobile unit. Desirably, the disclosed systems and methods may focus in particular on types of movements that relate to self locomotion, such as movements of the legs in kicking motions or simulated walking motions.

The systems and methods described herein are particularly suitable for advancing cognitive, perceptual and motor abilities of a user lacking natural mobility. Suitable users of the disclosed embodiments include children such as infants or toddlers having disorders that hinder development of self locomotion or mobility. Repeated use of the disclosed embodiments may desirably enable infants to learn that they how to maneuver the device and, thereby, explore their surroundings.

While the invention is described herein primarily with respect to use by infants who have not yet developed mobility, it will be understood that the invention is not so limited. The disclosed embodiments may be usable by any sort of user to control the mobility of the mobile unit. Additionally, while the invention is described herein primarily with respect to exploring of a reasonably flat environment through simple forward/backward movement, it will be understood that the invention is again not so limited. The disclosed embodiments may be usable to control any sort of movement, including, for example, climbing, crawling, swimming, jumping, or any other movements necessary to navigate particular embodiments.

An exemplary powered mobility system is described in U.S. patent application Ser. No. 12/245,169, entitled "POWERED MOBILITY FOR SPECIAL NEEDS CHILDREN," filed on Oct. 3, 2008, the contents of which are incorporated herein by reference in their entirety. Certain embodiments of the present invention may include a user interface, as described in the above-referenced application, usable in cooperation with the components described herein to generate and control mobility.

Figure 1:
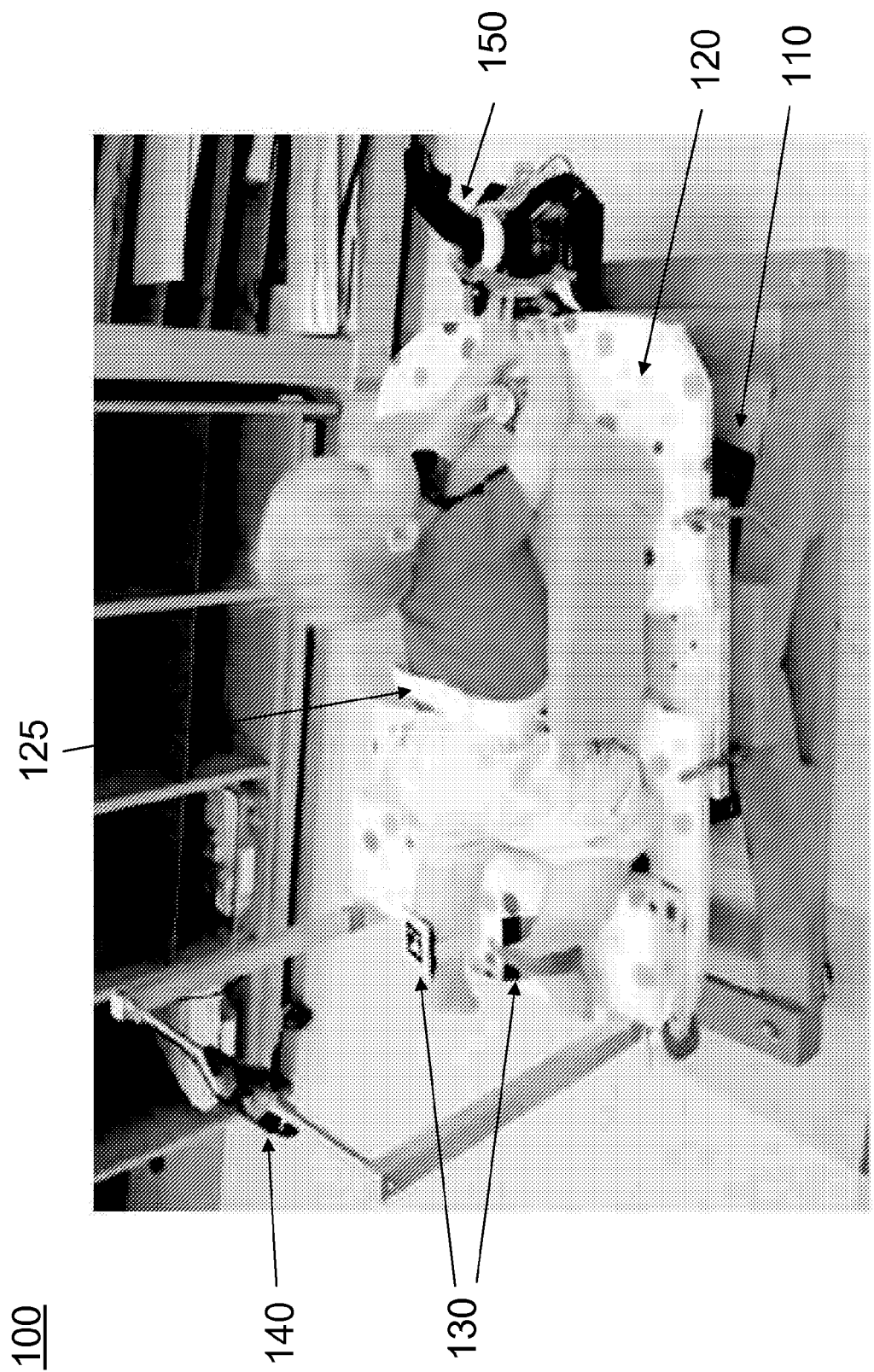
FIG. 1 is a diagram illustrating an exemplary powered mobility system in accordance with aspects of the present invention.
Figure 2:
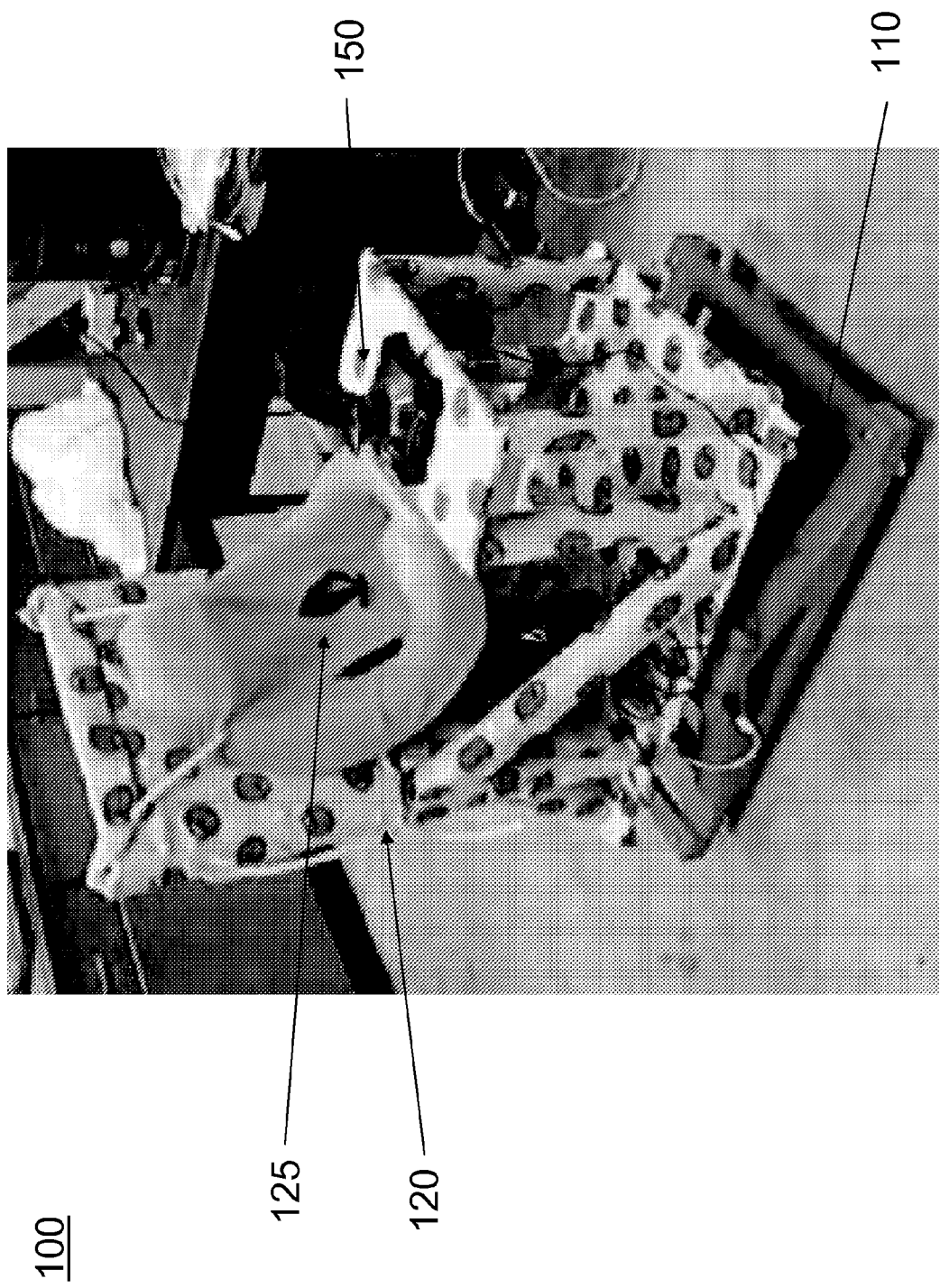
FIG. 2 is a diagram illustrating another exemplary powered mobility system in accordance with aspects of the present invention.

Referring now to the drawings, FIGS. 1 and 2 illustrate an exemplary powered mobility system 100 in accordance with aspects of the present invention. Powered mobility system 100 may be usable to assist a user that lacks natural mobility. As a general overview, powered mobility system 100 includes a mobile unit 110, a support frame 120, a plurality of markers 130, a motion capture device 140, and a data processor. Additional details of powered mobility system 100 are described herein.

Mobile unit 110 is operable to move powered mobility system 100. Mobile unit 110 may be operable to advance and/or retreat in a given direction, and may be operable to turn through 360° with little or no turning radius. Mobile unit 110 may include a self-contained power source (e.g., a battery) in order to power any movements without the necessity or restriction of connection to an external power source. Mobile unit 110 may also include a plurality of sensors (e.g., sonar sensors) on its periphery in order to detect objects that may be encountered during movement of powered mobility system 100. In an exemplary embodiment, mobile unit 110 is a drive assembly having a motor and multiple wheels. Suitable drive assemblies for use as mobile unit 110 include, for example, the Pioneer 3-DX robot from MobileRobots, Inc. of Amherst, N.H. Other suitable mobile units will be known to one of ordinary skill in the art from the description herein.

Support frame 120 is coupled to mobile unit 110. Support frame 120 is adapted to support a user of powered mobility system 100. Desirably, support frame 120 is sized to support an infant or small child user of powered mobility system 100. Support frame 120 may include an attachment mechanism 125 for securing the user to support frame 120. Attachment mechanism 125 may comprise any structure adapted to of secure the user without injury at any place along the user's body while enabling sufficient movement of the markers 130 for capture by motion capture device 140. Suitable attachment mechanisms 125 include, for example, a strap, belt, harness, or other structure adapted to encircle or be worn by the user to secure the user to support frame 120.

In one exemplary embodiment, support frame 120 comprises a platform, as shown in FIG. 1. The platform is configured to support the user of powered mobility system 100 in a prone position thereon. The platform may desirably include a pad to support the user's torso, so that the user is placed in a crawling position on support frame 120. When support frame 120 comprises a platform, attachment mechanism 125 may comprise one or more straps for securing the user to the platform, as shown in FIG. 1.

In another exemplary embodiment, support frame 120 comprises an upright stand, as shown in FIG. 2. The upright stand is configured to support the user of powered mobility system 100 in an upright position. When support frame 120 comprises an upright stand, attachment mechanism 125 may comprise a harness connected to upright stand for securing the user in the upright position, as shown in FIG. 2. The harness desirably allows the user's legs to hang freely, without direct attachment to support frame 120, such that the user can freely move his or her legs in a simulated walking motion.

It will be understood that support frame 120 is not limited to the above structures. Support frame 120 may comprise any structure that is able to hold a user in place as powered mobility system 100 moves. For example, support frame 120 may comprise a seat on which the user may be seated.

Markers 130 are configured to be attached to the user. Markers 130 may be attached anywhere on a user's body where the user is able to make detectable motions, including, for example, areas of the head, trunk, arms, legs, etc. Markers 130 may be attached to the user through any suitable connection such as, for example, buttons, straps, cords, belts, hook-and-loop fasteners, or other such connectors. Markers 130 are configured to be detected by motion capture device 140, in order to enable operation of powered mobility system 100 by the user. Thus, markers 130 may include reflective and or structural components that may be easily recognized by motion capture device 140 in six degrees of freedom (three translation and three orientational). A suitable marker 130 for use with the present invention is shown in FIG. 1. Other suitable markers 130 will be understood by one of ordinary skill in the art from the description herein.

Motion capture device 140 detects the movement of markers 130. Motion capture device 140 is programmed to identify the position and/or orientation of markers 130 on a real-time or periodic basis. Motion capture device 140 may comprise one or more cameras positioned to obtain images from the area of support frame 120. The one or more cameras may obtain images at optical, infrared, or ultraviolet wavelengths, for example, based on the construction of markers 130. The cameras may include or be in communication with software that enables recognition of markers 130 in the images obtained by the cameras. Suitable cameras will be understood by one of ordinary skill in the art from the description herein.

In an exemplary embodiment, markers 130 and motion capture device 140 are part of an augmented reality system. The augmented reality system is usable to build a virtual world or environment by first imaging the position and movement of real world objects using markers 130. One suitable augmented reality system is the ARToolKit open source software application.

The data processor controls the operation of powered mobility system 100. The data processor is in communication with mobile unit 110 and motion capture device 140. For example, the data processor is programmed to receive signals from motion capture device 140, translate these received signals into instructions for moving mobile unit 110, and transmit those instructions to mobile unit 110, in order to move powered mobility system 100. Further functionality of the data processor is set forth in greater detail below regarding the operation of powered mobility system 100. Suitable data processors will be known to one of ordinary skill in the art from the description herein. The data processor may further include data storage for storing data for use in controlling the operation of powered mobility system 100, or data obtained during the operation of powered mobility system 100. For example, the data processor may store information on the current position of powered mobility system 100, the path traveled by powered mobility system 100 during a usage cycle, the speed of powered mobility system 100 during the usage cycle, or other data that may be useful in analyzing the use of powered mobility system 100.

Powered mobility system 100 is not limited to the above components, but may include alternative or additional components, as would be understood by one of ordinary skill in the art.

For one example, powered mobility system 100 may include a user interface 150, as shown in FIGS. 1 and 2. User interface 150 is positioned to be manipulated by a user when the user is supported in support frame 120. The data processor may also be programmed to receive signals from user interface 150, translate these received signals into instructions for moving mobile unit 110, and transmit those instructions to mobile unit 110, in order to move powered mobility system 100. In an exemplary embodiment, user interface 150 is a commercially-available joystick that may be touched or grasped by the user during operation of powered mobility system 100. Alternatively, user interface 150 may be a touch screen, mouse, or other device adapted to receive input from a user.

Exemplary operations of powered mobility system 100 will now be described in accordance with aspects of the present invention.

In the embodiment shown in FIG. 1, support frame 120 of powered mobility system 100 is configured to support the user in a prone position. In this embodiment, the plurality of markers 130 may be configured to be attached to the legs of the user (e.g., via straps), and the motion capture device 140 may be suspended above the user. In particular, it may be desirable to attach markers 130 to the backs of the user's legs, to facilitate detection by motion capture device 140.

In an exemplary operation of powered mobility system 100 in accordance with this embodiment, the user makes a kicking motion, which correspondingly moves markers 130. Motion capture device 140 is configured to detect the movement of markers 130 caused by the kicking motion of the user. Upon detecting this movement, motion capture device 140 transmits a signal to the data processor. The signal may indicate, for example, which marker 130 has moved, an updated position and/or orientation of the marker 130, and/or a speed of the marker 130. With this information, the data processor generates instructions for operating mobile unit 110. For example, kicking of both legs by the user may correspond to an instruction to advance or retreat mobile unit 110 in a given direction. For another example, kicking of a single leg by the user may correspond to an instruction for turning mobile unit 110 in the direction of the leg being kicked. In any of these examples, the speed of movement of mobile unit 110 may be controlled to be proportional to the speed of the kicking motion of the user, or the extent of the movement of marker 130.

In the embodiment shown in FIG. 2, support frame 120 of powered mobility system 100 is configured to support the user in an upright position. In this embodiment, the user's legs may dangle freely below him or her. The plurality of markers 130 may be configured to be attached to the legs of the user (e.g., via straps), and the motion capture device 140 may be attached below the user (e.g., to the underside of the harness).

In an exemplary operation of powered mobility system 100 in accordance with this embodiment, the user makes a simulated walking motion, which correspondingly moves markers 130. The simulated walking motion may comprise moving the legs forward and backward while in an upright position, thereby mimicking the walking gait of a normally mobile person. Motion capture device 140 is configured to detect the movement of markers 130 caused by the simulated walking motion of the user. Upon detecting this movement, motion capture device 140 transmits a signal to the data processor. As stated above, the signal may indicate, for example, which marker 130 has moved, an updated position and/or orientation of the marker 130, and/or a speed of the marker 130. With this information, the data processor generates instructions for operating mobile unit 110. For example, a walking motion using both legs may correspond to an instruction to advance or retreat mobile unit 110 in a given direction. For another example, a walking motion with a single leg may correspond to an instruction for turning mobile unit 110 in the direction of the leg performing the walking motion. In any of these examples, the speed of movement of mobile unit 110 may be controlled to be proportional to the speed of the simulated walking motion of the user, or the extent of the movement of marker 130.

It will be understood that the example instructions set forth above with respect to both embodiments are not intended to limit the movement/instruction combinations that may be performed by powered mobility system 100. Other example movement/instruction combinations include: tracking hand/arm movement of the user with markers 130 to generate advance/retreat instructions for mobile unit 110; tracking head movement of the user with markers 130 to turn mobile unit 110; or tracking torso movement of the user with markers 130 to generate movement of mobile unit 110.

After the data processor has generated instructions, the data processor transmits the instructions to mobile unit 110, to operate the mobile unit to performed the desired movement in order to move powered mobility system 100.

When powered mobility system 100 includes user interface 150, the operation of powered mobility system 100 may be supplemented based on those additional signals. For example, the user may manipulate user interface 150 to generate an instruction to turn mobile unit 110, and may perform a kicking or simulated walking motion to advance or retreat mobile unit 110. Accordingly, the user may generate signals in multiple ways to control the movement of mobile unit 110.

By allowing a user of powered mobility system 100 to generate movement by recording movements of the user, powered mobility system 100 may enable users lacking natural mobility to more effectively explore and interact with their surroundings, and may enhance cognitive, perceptual, social, and/or emotional development.

Figure 3:
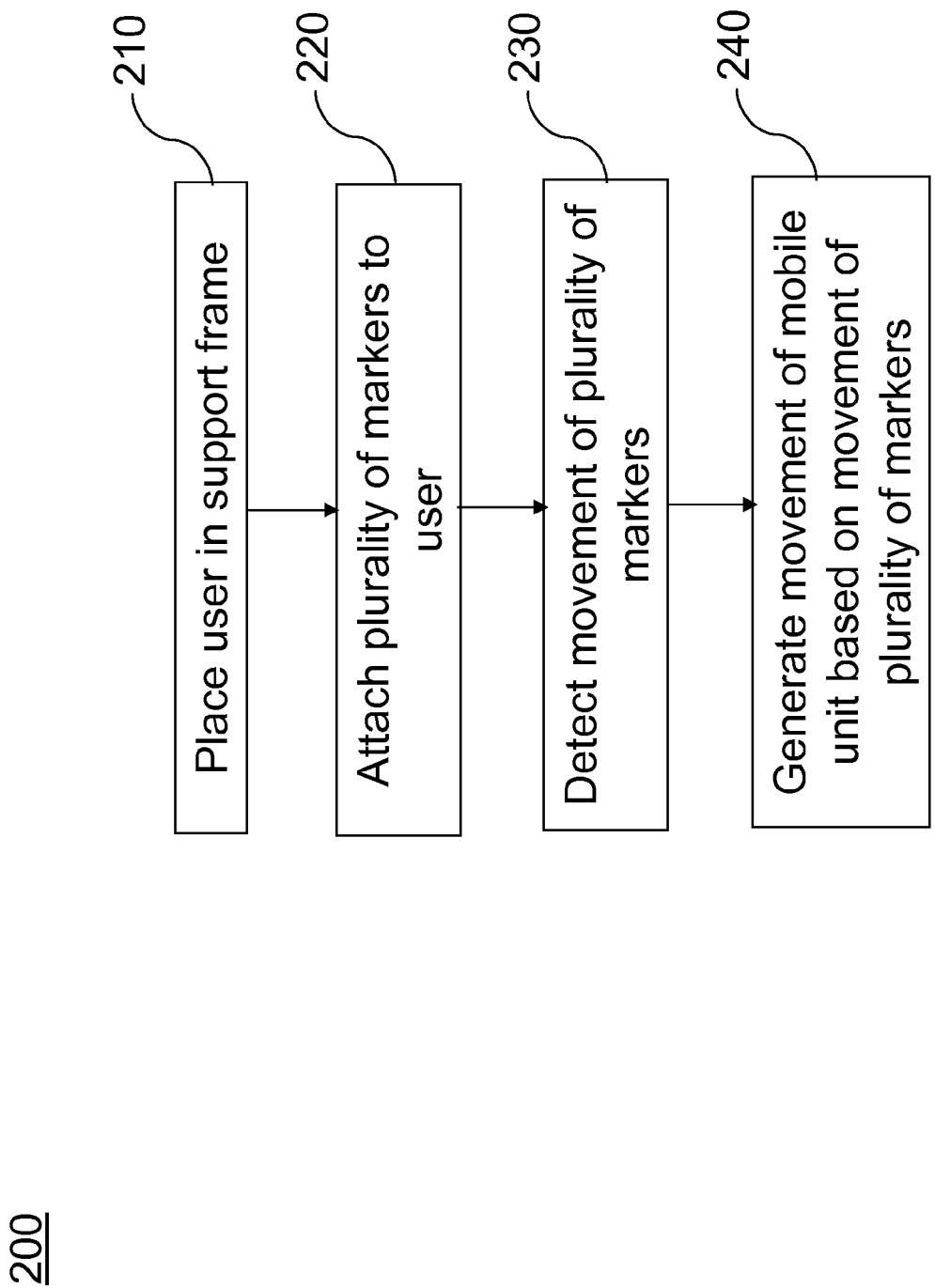
FIG. 3 is a flowchart illustrating an exemplary powered mobility method in accordance with aspects of the present invention.

FIG. 3 shows an exemplary powered mobility method 200 in accordance with aspects of the present invention. Powered mobility method 200 may be usable to assist a user that lacks natural mobility. As a general overview, powered mobility method 200 includes placing a user in a support frame, attaching a plurality of markers, detecting movement of the markers, and generating movement of a mobile unit. Additional details of method 200 are described herein with respect to the components of powered mobility system 100.

In step 210, a user is placed in a support frame. In an exemplary embodiment, the user is placed in support frame 120. Support frame 120 is coupled to mobile unit 110, which is operable to move support frame 120. In one preferred embodiment, the user may be placed in support frame 120 in a prone position, as shown in FIG. 1. In another preferred embodiment, the user may be placed in support frame 120 in an upright position, as shown in FIG. 2. The user may be an infant or small child. The user may be secured to support frame 120 by attachment mechanism 125.

In step 220, a plurality of markers are attached to the user. In an exemplary embodiment, markers 130 may be attached to the user through any of the connectors discussed above with respect to powered mobility system 100. As shown in FIG. 1, markers 130 may desirably be attached to the user's legs.

In step 230, movement of the markers is detected. In an exemplary embodiment, motion capture device 140 detects movement of markers 130 when markers 130 are attached to the user. Motion capture device 140 may detect the movement of markers 130 on a real-time or periodic basis. As set forth above, when the user is supported in the prone position, as shown in FIG. 1, motion capture device 140 may detect movement of markers 130 caused by a kicking motion of the user. Similarly, when the user is supported in the upright position, as shown in FIG. 2, motion capture device 140 may detect movement of markers 130 caused by a simulated walking motion of the user.

In step 240, movement of a mobile unit is generated based on the detected movement. In an exemplary embodiment, the data processor generates instructions for moving mobile unit 110 based on the movement of markers 130 detected by motion capture device 140. The instructions may include instructions to advance or retreat mobile unit 110, or turn mobile unit 110, based on kicking or simulated walking motions performed with one or both of the user's legs. After the instructions are generated, they may be transmitted to mobile unit 110 to generate the desired movement of mobile unit 110, in order to move powered mobility system 100.

Method 200 is not limited to the above steps, but may include alternative steps and additional steps, as would be understood by one of ordinary skill in the art from the description herein.

For one example, it may be desirable to vary the speed of movement of the mobile unit. Accordingly, method 200 may further include the step of determining a speed of the movement of the mobile unit. In an exemplary embodiment, the speed of movement of mobile unit 110 is determined based on the speed of the kicking or simulated walking motion performed by the user, or on the degree of movement of markers 130 by the user.

For another example, it may be desirable to receive more than one input from a user to control the movement of the powered orthosis system. Accordingly, method 200 may further include the step of detecting manipulation of a user interface. In an exemplary embodiment, the data processor detects movement of user interface 150. When the user manipulates user interface 150, the data processor may generate additional movement instructions for mobile unit 110 based on the manipulation of user interface 150 by the user. The instructions may include instructions to advance or retreat mobile unit 110, or turn mobile unit 110, based on a corresponding movement of user interface 150 by the user.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A powered mobility system comprising:
    a mobile unit operable to move the powered mobility system;
    a support frame coupled to the mobile unit, the support frame adapted to support a user of the powered mobility system;
    a plurality of markers configured to be attached to the user;
    a motion capture device configured to detect movement of the plurality of markers; and
    a processor in communication with the motion capture device, the processor programmed to receive signals from the motion capture device, translate the signals from the motion capture device into instructions for moving the mobile unit, and transmit the instructions to the mobile unit in order to move the powered mobility system.

2. The system of claim 1, wherein the support frame comprises an attachment mechanism for securing the user to the support frame.

3. The system of claim 1, wherein the support frame supports the user in a prone position.

4. The system of claim 3, wherein the plurality of markers are configured to be attached to legs of the user, and the motion capture device is configured to detect movement of the plurality of markers caused by a kicking motion of the user.

5. The system of claim 4, wherein the processor determines a speed of movement of the mobile unit based on a speed of the kicking motion of the user.

6. The system of claim 1, wherein the support frame supports the user in an upright position.

7. The system of claim 6, wherein the plurality of markers are configured to be attached to legs of the user, and the motion capture device is configured to detect movement of the plurality of markers caused by a simulated walking motion of the user.

8. The system of claim 7, wherein the processor determines a speed of movement of the mobile unit based on a speed of the simulated walking motion of the user.

9. The system of claim 1, wherein the instructions for moving the mobile unit comprise instructions for advancing or retreating the mobile unit in a given direction.

10. The system of claim 1, wherein the instructions for moving the mobile unit comprise instructions for turning the mobile unit.

11. The system of claim 1, further comprising a user interface positioned to be manipulated by a user supported in the support frame,
    wherein the processor is in communication with the user interface, and the processor is programmed to receive signals from the user interface, translate the signals from the user interface into additional instructions for moving the mobile unit, and transmit the additional instructions to the mobile unit in order to move the powered mobility system.

12. The system of claim 11, wherein the user interface comprises a joystick positioned to be touched or grasped by the user.

13. A powered mobility method comprising:
    placing a user in a support frame, the support frame coupled to a mobile unit operable to move the support frame;
    attaching a plurality of markers to the user;
    detecting movement of the plurality of the markers with a motion capture device when the plurality of markers are attached to the user; and
    generating movement of the mobile unit based on the movement of the plurality of the markers detected by the motion capture device.

14. The method of claim 13, wherein the placing step comprises:
    placing the user in a prone position in the support frame.

15. The method of claim 14, wherein
    the attaching step comprises attaching the plurality of markers to legs of the user, and the detecting step comprises detecting movement of the plurality of markers caused by a kicking motion of the user.

16. The method of claim 15, wherein further comprising the step of:
determining a speed of the movement of the mobile unit based on a speed of the kicking motion of the user.

17. The method of claim 13, wherein the placing step comprises:
placing the user in an upright position in the support frame.

18. The method of claim 17, wherein
the attaching step comprises attaching the plurality of markers to legs of the user, and
the detecting step comprises detecting movement of the plurality of markers caused by a simulated walking motion of the user.

19. The method of claim 18, wherein further comprising the step of:
determining a speed of the movement of the mobile unit based on a speed of the simulated walking motion of the user.

20. The method of claim 13, further comprising the steps of:
detecting manipulation of a user interface by the user; and
generating additional movement of the mobile unit based on the manipulation of the user interface by the user.

* * * * *